United States Patent [19]

Furihata

[11] 4,270,525

[45] Jun. 2, 1981

[54] SUCTION CONTROL DEVICE FOR AN ENDOSCOPE

[75] Inventor: Hiroyuki Furihata, Tokyo, Japan

[73] Assignee: Olympus Optical Co., Ltd., Tokyo, Japan

[21] Appl. No.: 28,678

[22] Filed: Apr. 10, 1979

[30] Foreign Application Priority Data

Apr. 17, 1978 [JP] Japan ............................... 53-44161
Apr. 17, 1978 [JP] Japan ........................... 53-50500[U]
Apr. 17, 1978 [JP] Japan ........................... 53-50501[U]

[51] Int. Cl.³ .............................................. A61B 1/00
[52] U.S. Cl. ..................................... 128/4; 128/276
[58] Field of Search ....................................... 128/3–9, 128/276–278

[56] References Cited

U.S. PATENT DOCUMENTS

| 3,726,272 | 4/1973 | Fukami et al. | 128/6 |
| 3,830,225 | 8/1974 | Shinnick | 128/4 X |
| 3,903,877 | 9/1975 | Terada | 128/6 |
| 3,958,566 | 5/1976 | Furihata | 128/4 |
| 4,198,958 | 4/1980 | Utsugi | 128/5 |

Primary Examiner—Robert W. Michell
Assistant Examiner—Arthur S. Rose

[57] ABSTRACT

A suction control device for an endoscope comprises a communication chamber communicating with a channel of an endoscope; an air chamber provided in the communication chamber and opening to the atmosphere; a communication hole connecting both chambers; a slider slidably disposed in the communication chamber and urged normally to such position as not to close the communication hole; a lid covering the slider; and a suction pipe communicating with the air chamber.

10 Claims, 8 Drawing Figures

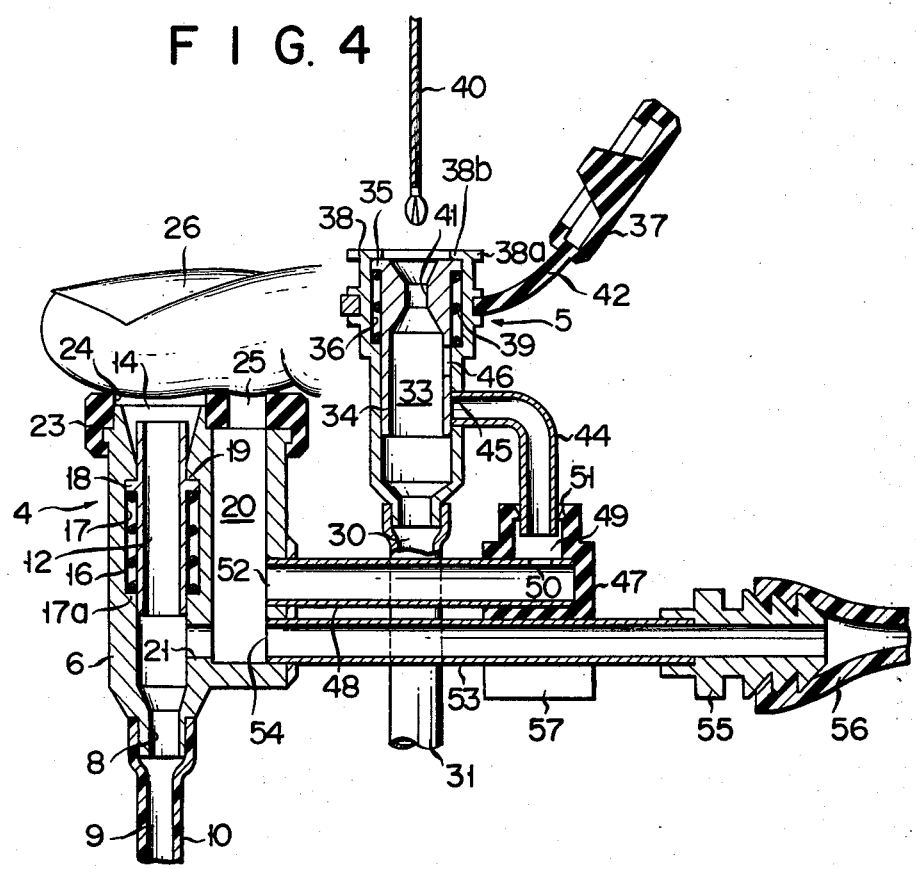
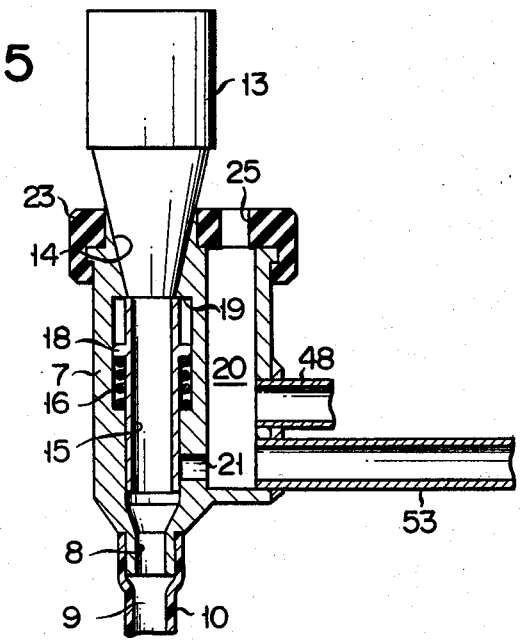

SUCTION CONTROL DEVICE FOR AN ENDOSCOPE

BACKGROUND OF THE INVENTION

This invention relates to a suction control device for an endoscope, which exerts a suction force in a channel of an endoscope when a medical instrument is not used and which does not exert a suction force in the channel while the medical instrument is used.

Generally, an endoscope is provided with a channel or channels through which a medical instrument such as a forceps is inserted into a body cavity or through which liquid medicine, water and air are supplied to the body cavity or body fluids are removed from the body cavity. While no medical instrument is inserted in the channel, particularly during a suction process, the proximal end of the channel should be closed to avoid an air leak. The proximal end of the channel is usually provided with a rubber valve having a slit. The slit is closed to minimize an air leak through the proximal end of the channel.

As the medical instrument such as a forceps is repeatedly inserted into, and withdrawn from, the channel, the valve is gradually worn, and the slit beomes broader and gradually fails to close the proximal end of the channel, and air will leak through the slit to reduce the suction force exerted in the channel.

SUMMARY OF THE INVENTION

An object of this invention is to provide a suction control device for an endoscope, which can exert a suction force in the channel of an endoscope when a medical instrument is not used and which does not provide a suction force in the channel when the medical instrument is used, thereby making it possible to insert the medical instrument through the channel into a body cavity, to apply the medical instrument to the channel, or to supply a fluid to the body cavity.

Another object of this invention is to provide a suction control device for an endoscope, which is provided with means for preventing an excessive air discharge from a body cavity, thereby to avoid hypoxia in the body cavity.

A further object of this invention is to provide an endoscope provided with a connector which holds a suction pipe and the communication means of a plurality of adaptors.

According to this invention there is provided a suction device for an endoscope, which comprises an adaptor and a suction pipe connected at one end thereto and at the other end to a suction device, said adaptor comprising;

an adaptor body connected to a proximal end of a channel extending through an endoscope;

a cylindrical communication chamber formed in the adaptor body and opening at one end to the channel and at the other end to the atmosphere;

a hollow cylindrical slider slidably inserted into the communication chamber and resiliently urged toward said other end of the communication chamber;

an air chamber formed in the adaptor body so as to open to the atmosphere at an adjacent portion thereof to said other end of the communication chamber and communicating at a remote portion thereof from said other end of the communication chamber with said suction pipe; and a communication hole formed in the adaptor body for communication between the communication chamber and the air chamber disposed in such a position that the communication hole is opened and closed by the slider according to movement thereof.

The suction control device further comprises a second adaptor comprising:

a second adaptor body connected to a proximal end of a second channel extending through an endoscope;

a cylindrical communication chamber formed in the second adaptor body and opening at one end to the second channel and at the other end to the atmosphere;

a hollow cylindrical slider slidably inserted into the communication chamber of the second adaptor body and resiliently urged toward said other end of the communication chamber of the second adaptor body;

a lid covering that portion of the second adaptor body at which said other end of the communication chamber of the second adaptor body toward said one end of the communication chamber of the second adaptor body;

a communication hole formed in a lateral wall of the slider;

communicating means so formed in the second adaptor body as aligns with the communication hole of the second adaptor body when the slider of the second adaptor body is moved toward said one end of the communication chamber of the second adaptor body, said communication means communicating with the air chamber of the first mentioned adaptor body.

BRIEF DESCRIPTION OF THE DRAWING

FIG. 4 shows how the device shown in FIG. 2 exerts a suction force in one of the channels and allows a medical instrument to be inserted into the other channel;

FIG. 5 illustrates how an injector is applied to a first adaptor body of the device shown in FIG. 2;

DESCRIPTION OF THE PREFERRED EMBODIMENTS

Figure 1:
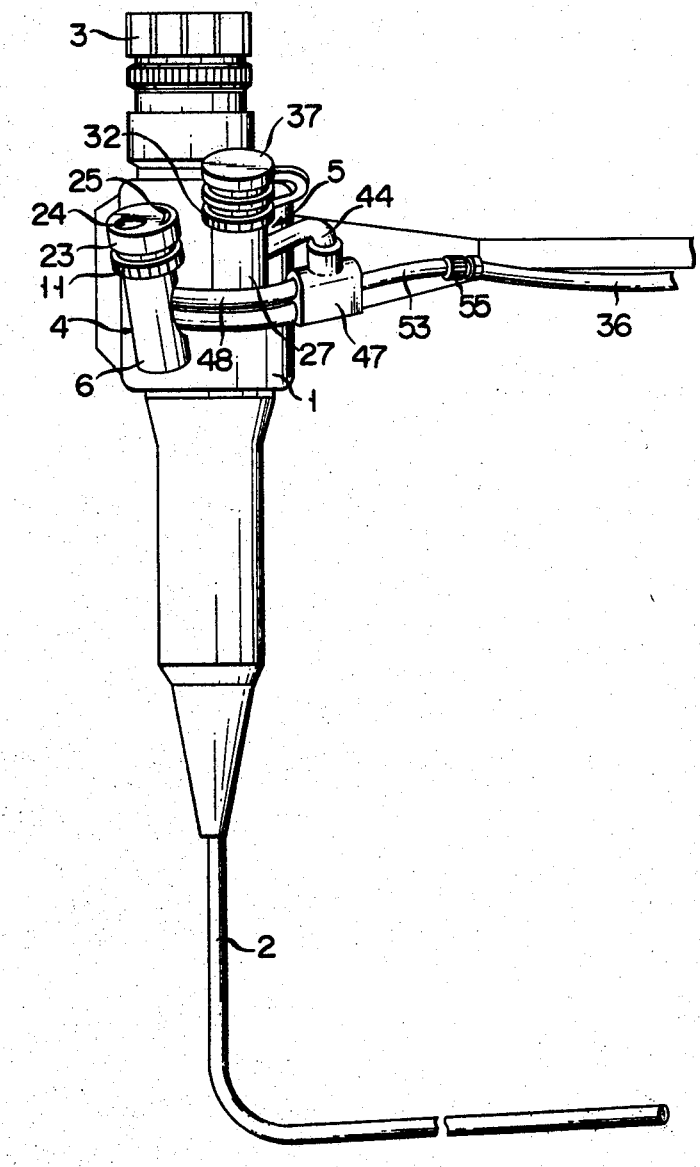
FIG. 1 is a perspective view of an endoscope provided with a suction control device according to this invention.

As shown in FIG. 1, a two-channel fiber bronchoscope (hereinafter referred to only as an "endoscope") has an operation unit 1 and a flexible sheath 2 to be inserted into the bronchus (or another body cavity). The operation unit 1 is provided with an ocular unit 3 on its top and a first adaptor 4 and a second adaptor 5 on its lateral side. Both adaptors 4 and 5 are attached to the operation unit 1. The first adaptor 4 is to inject a liquid medicine and to suck out a body fluid or air from the body cavity. Through the second adaptor 5 a medical instrument such as a forceps is inserted into the body cavity and withdrawn therefrom, or the body fluid or air is sucked out from the body cavity.

Figure 2:
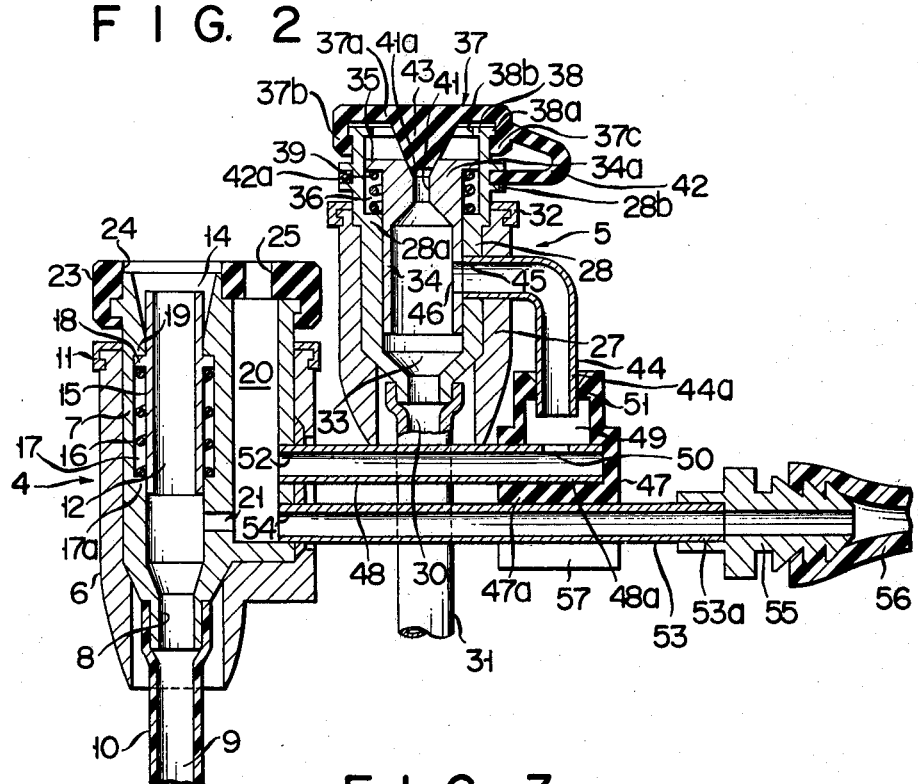
FIG. 2 is a cross sectional view of a suction control device according to this invention.

As FIG. 2 shows in detail, the first adaptor 4 comprises an adaptor housing 6 secured to the operation unit 1, a substantially hollow cylindrical adaptor body 7 inserted in the adaptor housing 6 and a bayonet element 11 coupling the adaptor body 7 to the housing 6. A cylindrical communication chamber 12 extend through the adaptor body 7. The lower end 8 of the communication chamber 12 communicates with the proximal end of a tube 10 which is made of plastic material such as polyethylene and polytetrafluoroethylene and which extends through the flexible sheath 2. The inner wall of the tube 10 defines a first channel 9 of the endoscope. The upper end of the communication chamber 12 is a funnel-shaped inlet 14 to receive the lower end of an injector 13 as shown in FIG. 5.

A hollow cylindrical slider 15 is inserted in the communication chamber 12. The slider 15 can slide axially of the adaptor body 7. The slider 15 is surrounded by a compression coil spring 16 which is disposed in an annular recess 17 formed in the outer periphery of the adaptor body 7. The lower end of the compression spring 16 abuts against the lower edge or seat 17a of the annular recess 17, and the upper end thereof pushes upward a flange 18 formed on the outer periphery of the slider 15. By the compression spring 16, the flange 18 is resiliently pressed against the upper edge or stop 19 of the annular recess 17. The upper end of the slider 15 therefore normally protrudes in the funnel-shaped inlet 14. Against the force of the compression spring 16, the slider 15 can be pushed into the communication chamber 12.

Formed in the adaptor body 7 is an air chamber 20 which extends parallel to the communication chamber 12 and which has a crescent cross section. Usually, the air chamber 20 communicates with the communication chamber 21 through a communication hole 12 which is formed in the adaptor body 7. The air chamber 20 is blocked completely from the communication chamber 12 when the slider 15 is pushed to its lowermost position.

The upper opening of the adaptor body 7 is covered with an end member 23 made of flexible material such as rubber. The end member 23 has openings 24 and 25 which communicate with the inlet 14 and the air chamber 20, respectively. The openings 24 and 25 are circular and crescent, respectively, according to the shapes of the cross section of the chambers 12 and 20. They are sized and spaced from each other such that they may be closed by the cushion of a finger at the same time.

The second adaptor 5 comprises an adaptor housing 27 secured to the lateral side of the operation unit 1, a substantially hollow cylindrical adaptor body 28 in the adaptor housing 27 and a bayonet element 32 coupling the adaptor body 28 to the housing 27. A cylindrical communication chamber 33 is formed in the adaptor body 28. The lower end portion of the communication chamber 33 has a diameter which is progressively smaller toward the lower end that is, it is conical-shaped. The lower end of the communication chamber 33 is connected to the proximal end of a tube 31 which is made of plastic material such as polyethylene and polytetrafluoroethylene and which extends through the flexible sheath 2. The interior of the tube 31 defines a second channel 30 of the endoscope.

A hollow cylindrical slider 34 is inserted in the communication chamber 33. The slider 34 can slide axially of the adaptor body 28. The slider 34 is surrounded by a compression coil spring 39 which is disposed in an annular recess 36 formed in the upper outer periphery of the adaptor body 28. The upper and lower ends of the compression spring 39 are pressed against a flange 35 formed on the upper end of the slider 34 and the lower edge or seat 28a of the annular recess 36, respectively, so that the spring 39 always urges the slider 34 upwards.

The upper end of the slider 34 comprises a thick portion 34a with a small central bore 41. The upper portion 41a of the bore 41 is shaped like a funnel. Through the bore 41 an elongated medical instrument such as a forceps is inserted as illustrated in FIG. 4.

The upper opening of the adaptor body 28 is covered with a lid 37 made of flexible material such as rubber. The lid 37 comprises a lid portion 37a, a skirt 37b and a truncated projection 43 extending from the central part of the inner surface of the lid portion 37a. When the upper end of the adaptor body 28 is covered with the lid 37, an outwardly extending portion 38a of a flange 38 formed on the upper end of the adaptor body 28 fits into a groove defined by the inner surface of the lid portion 37a and an inwardly extending flange 37c formed in the lower edge of the skirt 37b. The upper opening of the adaptor body 28 is therefore closed steadfastly. Further, the tip of the projection 43 is placed into the funnel-shaped portion 41a of the central bore 41, thus pushing the slider 34 to the lowermost position against the force of the compression coil spring 39. From the lateral side of the skirt 37b extends a string-like connecting portion 42, the free end of which is integrally connected by a ring 42a fitted in an annular groove in a flange 28b formed on the outer periphery of the adaptor body 28. The lid 37 remains connected to the adaptor body 28 even when it is uncovered from the upper end of the body 28. The connecting portion 42 and the ring 42a not only make it easy to close and open the upper end of the adaptor body 28 but also prevent the lid 27 from being lost.

A first connecting pipe 44 has one end 45 attached to the adaptor body 28. A communication hole 46 is formed in the lateral wall of the slider 34 such that the hole 46 opens to said one end 45 of the pipe 44 to allow the pipe 44 to communicate with the communication chamber 33 when the slider 34 is in the lowermost position (FIGS. 2 and 3) while the portion of the lateral wall of the slider 34 below the communication hole 46 closes said one end 45 of the connecting pipe 44 to block the pipe 44 from the communication chamber 33 when the slider 34 is raised to the uppermost position (FIG. 5).

The other end 44a of the first connecting pipe 44 is connected to a connector 47 made of elastic material such as rubber. It comprises a saddle-shaped body 47a and a hollow cylindrical body 51. A communication chamber 49 is provided partly in the saddle-shaped body 57a and partly in the hollow cylindrical body 51 and communicates with the other end 44a of the first connecting pipe 44.

A second connecting pipe 48 has one end 52 connected to the lateral wall of the adaptor body 7 of the first adaptor 4 so as to communicate with the air chamber 20. The other end 48a of the second connection pipe 48 is inserted into the saddle-shaped body 47a of the connector 47 and has a hole 50 through which it communicates with the communication chamber 49. Thus, the air chamber 20 of the adaptor body 7 of the first adaptor 4 communicates with the communication chamber 49 of the connector 47 by means of the second connecting pipe 48.

A suction pipe 53 is arranged in parallel below the second connecting pipe 48. One end 54 of the suction pipe 53 is connected to the lateral wall of the adaptor body 7 of the first adaptor 4 so as to communicate with the air chamber 20. An intermediate portion of the suction pipe 53 is held in a groove 57 formed in the lower portion of the saddle-shaped body 47a of the connector 47. The other end 53a of the suction pipe 53 is connected to a suction tube 56 by means of a connecting member 55 attached to the end 53a. The suction tube 56 is made of flexible plastic material such as vinyl chloride and polyurethane and is connected to a suction device (not shown).

As is cear from the above description, the connector 47 not only provides communication between the air chamber 20 in the adaptor body 7 of the first adaptor 4 and the communication chamber 33 in the adaptor body 28 of the second adaptor 5, but also holds the connecting pipes 44 and 48 and the suction pipe 53 together, thereby collecting these pipes for the easy operation of the endoscope.

Referring to FIGS. 2 to 5, it will now be described how the above-described suction control device operates.

Figure 3:
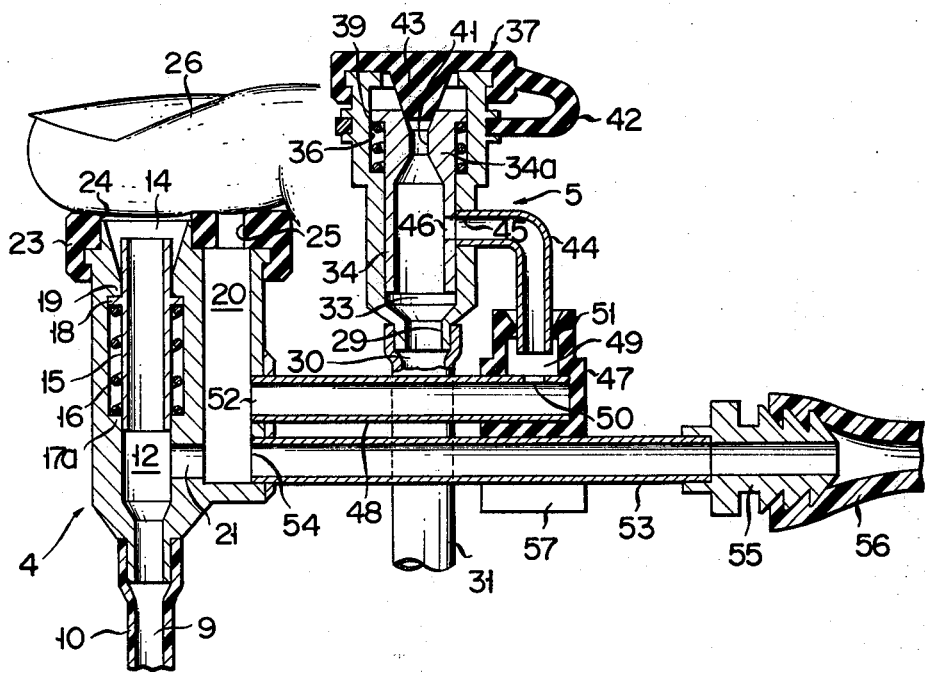
FIG. 3 shows how the device shown in FIG. 2 exerts a suction force in both channels of an endoscope.

As shown in FIG. 3, the openings 24 and 25 of the first adaptor 4 are covered with the cushion of a finger 26, and at the same time the upper end of the second adaptor 5 is covered with the lid 37 to connect the communication chamber 33 with the first connecting tube 44. When the suction device (not shown) is operated, a body fluid is sucked from a body cavity into the suction pipe 53 partly through the channel 9, the communication chamber 12, the communication hole 21 and the air chamber 20 and partly through the channel 30, the communication chamber 33, the communication hole 46 of the slider 34 in the lowermost position, the first connecting pipe 44, the communication chamber 49 in the connector 47, the second connecting pipe 48 and the air chamber 20 of the first adaptor 4. The body fluid is further led to the suction device (not shown) through the suction tube 56. Thus, the body fluid is sucked into the suction device via both the channels 9 and 30 of the endoscope.

When the lid 37 is uncovered as shown in FIG. 4, the slider 34 is raised by the spring 39 till it contacts the inwardly extending portion 38b of the flange 38 of the adaptor body 28. As a result, the slider 34 closes the end 45 of the first connection pipe 44, thus effecting disconnection between the communication chamber 33 and the first connecting pipe 44. As the suction device (not shown) is operated while the openings 24 and 25 of the first adaptor 4 are kept closed by the finger cushion, the body fluid is sucked from the body cavity to the suction device through the first channel 9 in such a route as described above with reference to FIG. 3. Since the body fluid is not sucked through the second channel 30, a medical instrument 40 such as a forceps can be inserted through the central bore 41, the communication chamber 33 and the second channel 30 into a required portion of the body cavity while the sucking operation is carried out or not carried out by the first adaptor 4.

To inject a liquid medicine (e.g. anesthetic, physiological salt solution etc.) into a body cavity through the first channel 9, the suction control device is operated as illustrated in FIG. 5. First, an injector 13 is fitted into the funnel-shaped inlet 14 of the first adaptor 4 and lowers the slide 15 to block the communication hole 21. The air chamber 20 is isolated from the communication chamber 12. Consequently, the liquid medicine can be injected only through the first channel 9 without leaking into the suction tube 53.

In the above-described embodiment of this invention, the adaptor bodies 7 and 28 and their associated parts can be detached from the operation unit 1.

When liquid medicine injection, fluid suction or instrument insertion is carried out, the suction control device is in such a state as illustrated in FIG. 2. Generally, even while the device is in this state, the suction device (not shown) is operated. In case the suction control device is applied to a two-channel fiber bronchoscope, however, the patient may experience hypoxia if the suction device sucks too much air through the distal end of the bronchoscope. The chamber 20 is used for avoiding this disadvantage. Most amount of air to be sucked is conducted from the chamber 20 and the remaining air is sucked from the bronchi such that the sucking of the remaining air produces a negative pressure high enough to suck up a body fluid but not so high as to cause hypoxia in the body cavity, e.g. the bronchi.

Figure 6:
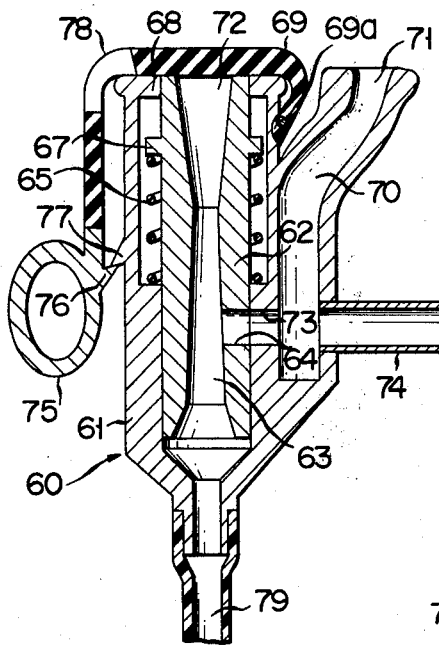
FIG. 6 is a cross sectional view of another embodiment of an adaptor with its opening closed with a lid.
Figure 7:
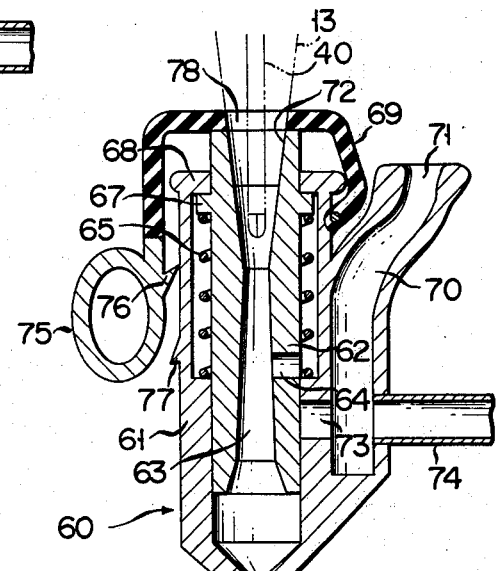
FIG. 7 is a cross sectional view of the adaptor shown in FIG. 6, with a medical instrument inserted into a channel of an endoscope.

FIGS. 6 and 7 show another embodiment of this invention. A suction control device comprises a single adaptor 60, through which a liquid medicine can be injected into and sucked up from a body cavity and through which a medical instrument can be inserted thereinto and withdrawn therefrom. The adaptor 60 comprises a substantially hollow cylindrical adaptor body 61 and a hollow cylindrical slider 62 slidably disposed in the adaptor body 61. The slider 62 is provided with a central communication chamber 63 and has a communication hole 64 in its lateral wall. An outwardly extending flange 67 is integrally formed on the upper end portion of the slider 62. The slider 62 is urged upwardly by a compression spring 65 so that the flange 67 contacts and upwardly presses an inwardly extending flange 68 integrally formed on the upper end of the adaptor body 61. The slider 62 is lowered to the lowermost position when a strip-shaped lid 69 made of flexible material such as rubber covers the top of the adaptor body 61.

The adaptor body 61 has an air chamber 70 arranged parallel with the communication chamber 63 and opens at an opening 71 to the atmosphere. The opening 71 and an inlet 71 of the slider 62 are positioned on the same plane and so close to each other that they may be blocked by the cushion of a finger at the same time. The adaptor body 61 has a communication hole 73 which opens the air chamber 70. The hole 73 communicates with the communication hole 64 of the slider 62 to allow the air chamber 70 to communicate with the communication chamber 63 when the slider 62 is lowered to its lowermost position. In other words, when the lid 69 covers the top of the adaptor body 61, communication is made between the communication chamber 63 and the air chamber 70. When the lid 69 is removed from the top of the adaptor body 61 the slider 62 is raised to the uppermost position to block upwards the communication hole 64. Thus, the communication chamber 30 is disconnected from the air chamber 70.

A suction pipe 74 is connected to a lower portion of the air chamber 70. When the opening 71 is left open, air flows into the suction pipe 74 through the opening 71 and the air chamber 70, whereby any fluid cannot be sucked from the body cavity through a channel 79 of an endoscope and the communication chamber 63. On the other hand, when the opening 71 is closed by the cushion of a finger, a fluid can be sucked from the body cavity through the channel 79 and the chamber 63.

The lid 69 has one end 69a pivoted to the adaptor body 61. The other end of the lid 69 is provided with an engaging portion 75 having a claw or detent 76. When the claw 76 engages a claw or detent 77 integrally formed on the lateral wall of the adaptor body 61, the lid 69 covers the top of the adaptor body 61.

As mentioned above, when the lid 69 is placed on the top of the adaptor body 61, it lowers the slider 62 to bring the hole 64 into communication with the hole 73 and there is effected communication between the communication chamber 63 and the suction pipe 74. As a result, a suction force can be exerted in the channel 79 by operating a suction device (not shown) which is connected to the suction pipe 74.

When the claw 75 is released from the claw 77, the slider 62 is raised by the spring 65 until its flange 67 contacts the flange 68 of the adaptor body 61 as illustrated in FIG. 7, and a hole 78 made in the lid 69 is positioned to align with the inlet 72 of the slider 62. As shown by the chain lines in FIG. 7, the tip end portion of the injector 13 is inserted into the inlet 72 through the hole 78, or the other medical instrument such as a forceps 40 is inserted into the channel 79 through the hole 78, communication chamber 63 and the channel 79. Since the communication hole 73 is closed by the slider 62, neither the communication chamber 63 nor the channel 79 communicates with the suction pipe 74. Consequently, no suction force is exerted in the channel 79 while a medical instrument is inserted in the slider 62, or the slider 62 and the channel 79.

Figure 8:
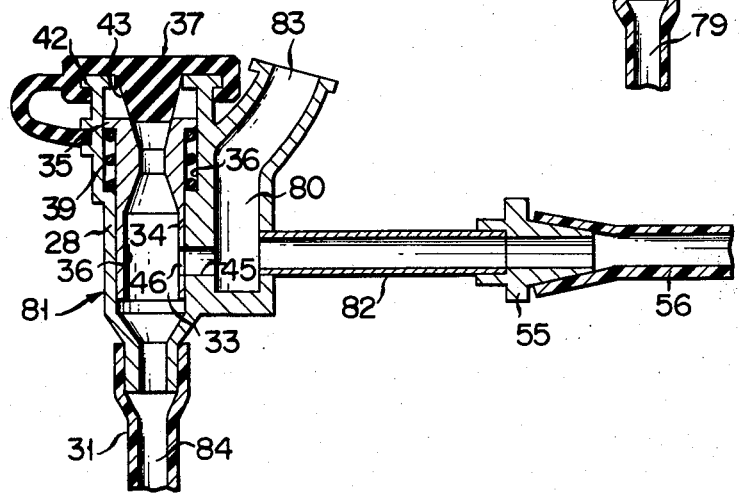
FIG. 8 is a cross sectional view of a further embodiment of an adaptor.

FIG. 8 shows still another embodiment of this invention. The suction control device comprises a single adaptor 81. The adaptor 81 is similar to the second adaptor 5 of the embodiment shown in FIGS. 2 to 5 but differs in that it is provided with an air chamber 80 formed in an adaptor body 28 in parallel with a central communication chamber 33 and that a suction pipe 82 is connected to the bottom of the air chamber 80. Where the upper end of the adaptor 81 and the opening 83 of the air chamber 80 are closed with a lid 37 and a finger cushion, respectively, a suction force can be applied in a channel 84 of an endoscope. When the lid 37 is removed from the top of the adaptor body 28, a slider 34 is raised by a spring 39 to disconnect a communication chamber 33 in the adaptor body 28 from the suction pipe 82, whereby a liquid medicine can be injected or a medical instrument such as a forceps can be inserted into the channel 84 without exerting a suction force in the channel 84.

What is claimed is:

1. In an elongated endoscope having two ends and two channels extending through the endoscope, each of said channels having two ends, a suction control device communicating with one of said channels and for communication with a suction device disposed externally of the endoscope, said suction control device comprising:
    an adaptor comprising an adaptor body provided on one end of the endoscope, a cylindrical communication chamber formed in the adaptor body and having two ends, one end of said chamber communicating with one end of one of said channels and the other end being open to the atmosphere, a hollow cylindrical slider slidable axially in the communication chamber, an urging means disposed in the communicating chamber for urging the slider toward the other end of the communication chamber, and a lid, said lid having means for pushing the slider toward said one end of the communication chamber when the lid covers the other end of the communication chamber;
    air conducting means provided on said one end of the endoscope and including an air chamber communicating with the atmosphere;
    communication means disposed between the air conducting means and the communication chamber for allowing the air chamber to communicate with said one end of the communication chamber when the lid covers the other end of the communication chamber and pushes the slider toward said one end of the communication chamber; and
    a suction pipe disposed between the air conducting means and the suction device for allowing the air chamber to communicate with the suction device.

2. The device according to claim 1, wherein said lid has a connecting portion for joining the lid to the adaptor body.

3. The device according to claim 1, wherein said lid comprises a strip-shaped member made of flexible material one end of which is pivoted to the adaptor body and the other end of which is provided with engaging means, and said adaptor body is provided on an outer periphery thereof with engaging means engageable with the engaging means of the lid, said slider being moved toward said one end of the communication chamber when both the engaging means engage each other.

4. The device according to claim 3, wherein there is provided a medical instrument leading hole at that portion of the lid which is aligned with the communication hole of the adaptor body when both the engaging means are disengaged from each other.

5. The device according to claim 4, wherein each of said engaging means comprises a claw.

6. The device according to claim 1 further including a second adaptor which comprises:
    a second adaptor body provided on said one end of the endoscope;
    a second cylindrical communication chamber formed in the second adaptor body and having two ends, one end of said second communication chamber communicating with one end of the other channel and the other end of said second communication chamber being open to the atmosphere;
    said air conducting means constituting part of the second adaptor body and said air chamber having an elongated configuration and extending in parallel with the second communication chamber in the second adaptor body, said air chamber communicating with said one end of the second communicating chamber;
    a second hollow cylindrical slider slidable axially in the second communication chamber and adapted to block the second communication chamber from the air chamber when the second slider is moved to said one end of the second communication chamber; and
    a second urging means disposed in the second communication chamber for urging the second slider toward the other end of the second communication chamber.

7. The device according to any one of claims 2, 1 and 6, wherein said means for pushing said slider is a projection on said lid extending toward said one end of the first-mentioned communication chamber for pushing the first-mentioned slider toward said one end of the first-mentioned communication chamber to allow the first-mentioned slider to block the first-mentioned communication chamber.

8. The device according to claim 6, wherein said second adaptor further comprises an elastic end member mounted on the second adaptor body and having a first opening for permitting the second communication chamber to communicate with the atmosphere and a second opening disposed adjacent to said first opening for permitting the air chamber to communicate with the atmosphere.

9. The device according to claim 6, wherein said communication means comprises a first connecting pipe having two ends, one end of said first connecting pipe being connected to the first-mentioned adaptor body so as to communicate with the communication chamber of the first-mentioned adaptor body, a second connecting pipe having two ends, one end of said second connecting pipe being connected to the second adaptor body so as to communicate with the air chamber, and a connector connecting the other end of the first-connecting pipe to the other end of the second connecting pipe, said connector having a connecting chamber for effecting communication between the first-connecting pipe and said communication chamber.

10. The device according to claim 9, wherein said connector is provided with a groove for holding the suction pipe.

* * * * *